(12) United States Patent
Shafiee

(10) Patent No.: US 10,417,481 B2
(45) Date of Patent: Sep. 17, 2019

(54) HOME EVALUATION OF THE QUALITY OF SEMEN SAMPLES

(71) Applicant: THE BRIGHAM AND WOMEN'S HOSPITAL, INC., Boston, MA (US)

(72) Inventor: Hadi Shafiee, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 15/739,236

(22) PCT Filed: Jun. 22, 2016

(86) PCT No.: PCT/US2016/038739
§ 371 (c)(1),
(2) Date: Dec. 22, 2017

(87) PCT Pub. No.: WO2016/209943
PCT Pub. Date: Dec. 29, 2016

(65) Prior Publication Data
US 2018/0181792 A1 Jun. 28, 2018

Related U.S. Application Data

(60) Provisional application No. 62/182,666, filed on Jun. 22, 2015.

(51) Int. Cl.
*G06T 7/13* (2017.01)
*G06K 9/00* (2006.01)
(Continued)

(52) U.S. Cl.
CPC .... *G06K 9/00127* (2013.01); *B01L 3/502715* (2013.01); *C12N 5/0612* (2013.01);
(Continued)

(58) Field of Classification Search
CPC .......... G06K 9/00127; B01L 3/502715; C12N 5/0612
See application file for complete search history.

(56) References Cited

U.S. PATENT DOCUMENTS 4,276,139 A * 6/1981 Lawson ................. A61D 19/00
204/DIG. 5
5,605,803 A 2/1997 Herr et al.
(Continued)

FOREIGN PATENT DOCUMENTS

EP 2522981 A1 11/2012
WO 00/30051 A1 5/2000
(Continued)

OTHER PUBLICATIONS

International Search Report for Application No. PCT/US2016/038739 dated Sep. 7, 2016.
(Continued)

*Primary Examiner* — Thai Q Tran
*Assistant Examiner* — Jose M Mesa
(74) *Attorney, Agent, or Firm* — Tarolli, Sundheim, Covell & Tummino LLP

(57) ABSTRACT

Systems and methods are provided for evaluating the quality of a semen sample at a mobile device. An assembly includes an optical assembly with at least one lens and a housing configured to engage with the mobile device such that an axis of the optical assembly is substantially aligned with a camera of the mobile device. The optical assembly is contained within the housing. A microfluidic chip includes a reservoir to hold the semen sample. The microfluidic chip engages with the housing such that the reservoir is aligned with the axis of the optical assembly.

17 Claims, 2 Drawing Sheets

(51) Int. Cl.
  *C12N 5/071* (2010.01)
  *B01L 3/00* (2006.01)
  *G01N 33/569* (2006.01)
  *H04N 5/225* (2006.01)

(52) U.S. Cl.
  CPC ......... *G01N 33/56966* (2013.01); *G06T 7/13* (2017.01); *H04N 5/2254* (2013.01); *H04N 5/2256* (2013.01); *B01L 2200/025* (2013.01); *B01L 2200/0647* (2013.01); *B01L 2300/0654* (2013.01); *B01L 2300/16* (2013.01); *B01L 2400/0487* (2013.01); *G01N 2400/40* (2013.01); *G01N 2800/367* (2013.01)

(56) References Cited

U.S. PATENT DOCUMENTS

| | | | |
|---|---|---|---|
| 5,866,354 A * | 2/1999 | Froman | C12Q 1/02 422/50 |
| 5,897,988 A | 4/1999 | Huszar | |
| 6,391,654 B1 | 5/2002 | Bateman | |
| 8,999,654 B2 | 4/2015 | Gaitanaris et al. | |
| 2002/0068358 A1 * | 6/2002 | Campbell | A01K 45/007 435/289.1 |
| 2003/0210835 A1 * | 11/2003 | Horbaschek | G06T 5/50 382/302 |
| 2004/0146850 A1 * | 7/2004 | Aravanis | B01L 3/502715 435/4 |
| 2005/0112541 A1 * | 5/2005 | Durack | C12N 5/0612 435/2 |
| 2006/0060769 A1 * | 3/2006 | Bousse | B05B 5/025 250/282 |
| 2006/0139746 A1 | 6/2006 | Delaage et al. | |
| 2008/0318250 A1 | 12/2008 | Gilmer et al. | |
| 2012/0052485 A1 | 3/2012 | Shany et al. | |
| 2013/0045890 A1 | 2/2013 | Jensen et al. | |
| 2013/0260452 A1 * | 10/2013 | Toner | A01N 1/0268 435/307.1 |
| 2014/0339445 A1 * | 11/2014 | Sharpe | G01N 15/1459 250/574 |
| 2014/0348197 A1 * | 11/2014 | Freund | H01L 33/58 372/50.23 |
| 2015/0024385 A1 * | 1/2015 | Parrish | C12N 5/061 435/6.1 |
| 2015/0300932 A1 | 12/2015 | Schaff et al. | |
| 2016/0067375 A1 * | 3/2016 | Holmes | A61L 27/18 623/23.58 |
| 2016/0067710 A1 | 3/2016 | Larsen et al. | |
| 2017/0109879 A1 * | 4/2017 | Urbano | G06T 7/0012 |

FOREIGN PATENT DOCUMENTS

| | | |
|---|---|---|
| WO | 2001/060968 A1 | 8/2001 |
| WO | 2004/053465 A2 | 6/2004 |
| WO | 2009/043393 A1 | 4/2009 |
| WO | 2009/116051 A1 | 9/2009 |
| WO | 2013/158506 A2 | 10/2013 |
| WO | 2014/055559 A1 | 4/2014 |
| WO | 2015/077333 A1 | 5/2015 |
| WO | 2015/087232 A1 | 6/2015 |

OTHER PUBLICATIONS

Extended European Search Report for corresponding European Application Serial No. 16815209.8, dated Dec. 21, 2018, pp. 1-7.

* cited by examiner

HOME EVALUATION OF THE QUALITY OF SEMEN SAMPLES

RELATED APPLICATIONS

The present invention is a U.S. National Stage under 35 USC 371 patent application, claiming priority to Serial No. PCT/US2016/038739, filed on 22 Jun. 2016; which claims priority of U.S. 62/182,666, filed on 22 Jun. 2015, the entirety of both of which are incorporated herein by reference.

TECHNICAL FIELD

This invention relates to medical systems, and more particularly, to home evaluation of the quality of semen samples.

BACKGROUND

There are more than seventy million infertile couples worldwide. Approximately one in every four infertile couples seek clinical treatment, where male factor accounts for about fifty percent of the infertility cases. The most important factors for male infertility include low sperm count and motility and sperm abnormality, which reduce the ability of sperm cells for oocyte fertilization. Assisted reproductive technologies (ARTs) such as in vitro fertilization (IVF), intracytoplasmic sperm injection (ICSI), and intrauterine insemination (IUI) are generally utilized in reproductive clinics to treat infertile couples. With an increasing rate of male infertility due to environmental and physiological conditions, there is an ever growing need for the use of ARTs in reproductive clinics.

There are four main factors which semen analysis tests examine: sperm concentration, sperm morphology, motility, and progressive motility. Sperm concentration tests examine the concentration of sperm in one milliliter (mL) of semen (approximately 20 million sperms/mL) though sperm concentration is not an accurate indicator of a male's ability to reproduce. Males with a low sperm count can still reproduce, and males with high sperm counts can have difficulty. This discrepancy is due to sperm motility, a crucial factor which controls how capable the sperm is of entering an oocyte. Sperm motility, the movement of sperm, must be past a certain threshold in order for the sperm to successfully be able to swim up the female vaginal tract and penetrate the oocyte's hard outer shell. Seminal quality is evaluated by determining the percentage of motile sperm cells and the relative velocity of progressively motile sperm cells in a sample. The progressive motility of a sperm is a fundamental working characteristic that controls its ability to enter into both cervical mucus and the oocyte vestments.

SUMMARY OF THE INVENTION

In accordance with an aspect of the present invention, an assembly is provided for evaluating the quality of a semen sample at a mobile device. The assembly includes an optical assembly with at least one lens and a housing configured to engage with the mobile device such that an axis of the optical assembly is substantially aligned with a camera of the mobile device. The optical assembly is contained within the housing. A microfluidic chip includes a reservoir to hold the semen sample. The microfluidic chip engages with the housing such that the reservoir is aligned with the axis of the optical assembly.

In accordance with another aspect of the present invention, a method is provided for evaluating the quality of a semen sample. The semen sample is loaded into a microfluidic chip. The microfluidic chip is inserted into an optical assembly. The optical assembly is placed onto a mobile device such that an optical axis of the optical assembly is aligned with a camera of the mobile device. The camera is instructed to capture video of the semen sample through the optical assembly. A plurality of individual sperms are identified within each of a plurality of frames of the video. Associated paths are mapped for a subset of the plurality of individual sperms across the plurality of frames of the video.

In accordance with yet another aspect of the present invention, a system is provided for evaluating the quality of a semen sample. The system includes an optical assembly with at least one lens and a microfluidic chip including a reservoir to hold the semen sample and configured to engage with the optical assembly such that the reservoir is aligned with the optical axis of the optical assembly. A mobile device includes a camera aligned along the optical axis of the optical assembly, a processor, and a non-transitory computer readable medium storing executable instructions for evaluating a sperm quality from video captured at the camera. The executable instructions include a camera interface configured to instruct the camera to capture the video and a sperm recognition component configured to identify a plurality of individual sperms within each of a plurality of frames of the video. A sperm tracking component is configured to map associated paths for a subset of the plurality of individual sperms across the plurality of frames of the video.

DETAILED DESCRIPTION

Figure 1:
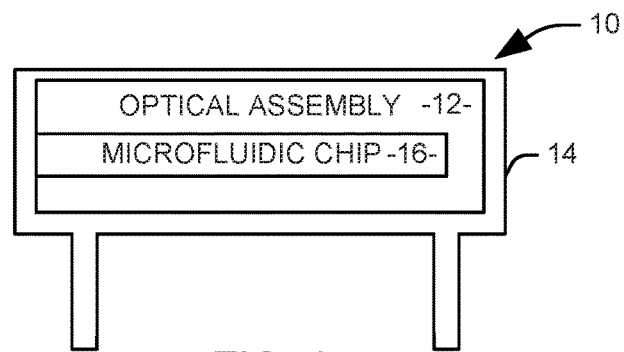
FIG. 1 illustrates an assembly for evaluating the quality of a semen sample at a mobile device.

In accordance with an aspect of the present invention, a point-of-care system for evaluating the quality of a semen sample with a mobile device is provided. Men often feel embarrassed to go to urologists, and women carry the weight with regard to infertility. Such behavior and reluctance has created a significantly large market for home-based male infertility tests. Furthermore, healthcare disparities: economic, cultural, societal, geographic, and religious, are major impediments to accessing infertility care worldwide. Infertility in resource-limited settings is a global issue. In addition, while sperm abnormalities are definitive markers for male infertility, they have also been linked to other medical conditions such as diabetes, thyroid disease, Cushing syndrome, liver or kidney disease, and chronic anemia in men. They may also be related to environmental effects and lifestyle effects such as due to smoking, medications, and dietary habits. Accordingly, by facilitating access to point of care evaluation of semen quality, the claims systems and methods can assist in early detection of these disorders.

Manual microscopy based testing and computer-assisted semen analysis (CASA) systems are the current standard methods to measure semen quality, but these methods are labor-intensive, expensive, and laboratory-based. The CASA technique requires highly trained technicians for producing reliable and repeatable results. It also requires bulky microscopy based image analysis systems that significantly limit its point-of-care applications in clinical settings, stud farming, and animal breeding. A majority of fertility clinics and small hospitals, including as many as ninety eight percent in the United States, do not possess CASA platforms available in the market and so use a less accurate and subjective manual method for semen analysis. Manual test results are subjective making it difficult to compare results from different clinics.

Turbidimetry, photon correlation spectroscopy, laser Doppler velocimetry, impedance-based, and holography-based analysis are also used for semen analysis. However, these methods are far from being inexpensive or portable and have not been adopted for home-based or clinical use for semen quality check. Some of these methods only provide sperm concentration and not motility which is an important factor for semen quality check. The lens-free holography-based method involves a complex image reconstruction and processing that is done on a computer connected to the developed device. It also requires a relatively expensive CMOS or CCD sensor that may not be appropriate for home-based or office-based portable semen analysis. Commonly used portable and home-based fertility assays in the market are FertilMARQ and SpermCheck that are colorimetric analyses that use a chemical staining approach for detecting sperm-specific proteins on the sperm head. However, these assays can only measure sperm concentration and not sperm motility.

The systems and methods described herein provide a simple, rapid, inexpensive, home-based male infertility test can shift the paradigm in infertility diagnosis and management in both developed and developing countries. This private, fast, and inexpensive point-of-care test can help men to remotely monitor their fertility potency without the need to go to fertility clinic for a semen analysis.

FIG. 1 illustrates an assembly 10 for evaluating the quality of a semen sample at a mobile device. The assembly 10 includes an optical assembly 12 comprising at least one lens. In one implementation, the optical assembly 12 includes a light source, such as an LED light, a power source for the light source, and two aspheric lenses, arranged to form an optical path along an optical axis of the assembly. The optical assembly can be located contained within a housing 14 configured to engage with the mobile device such that an axis of the optical assembly is substantially aligned with a camera of the mobile device. In one implementation, the housing 14 can include a plurality of leg members configured to space the optical assembly 12 from the camera by a focal length of the at least one lens. In another implementation, the housing 14 can include extensions on opposite sides of the device to mechanically affix the optical assembly 12 and housing 14 to the mobile device.

The optical assembly 12 can be configured to receive a microfluidic chip 16 comprising a reservoir configured to hold the semen sample. The microfluidic chip 16 is configured to engage with the housing such that the reservoir is aligned with the axis of the optical assembly. Accordingly, when the microfluidic chip 16 and the house 14 are in place, the light source will provide trans illumination to the semen sample, and the resulting light will be focused by the at least one lens onto a camera of the mobile device. Captured video of the semen sample can then be used for analysis.

Figure 2:
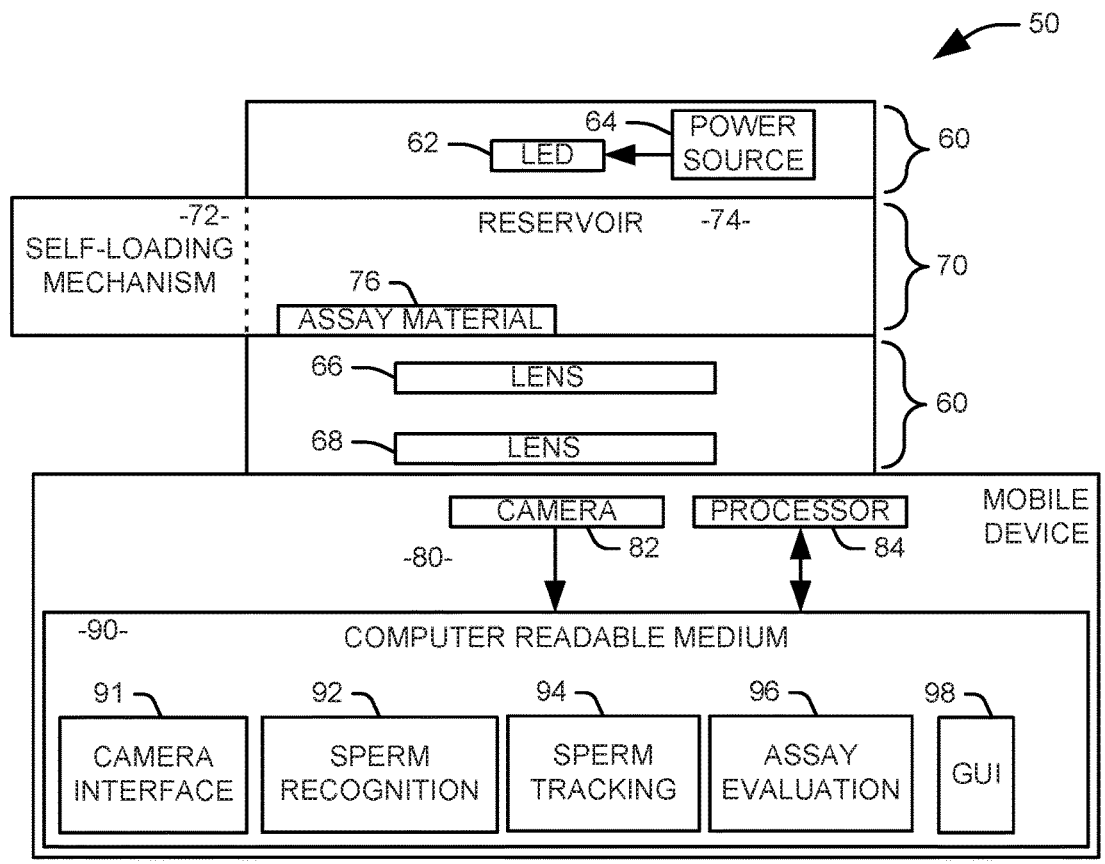
FIG. 2 illustrates one example of a system for evaluating the quality of a semen sample.

FIG. 2 illustrates one example of a system 50 for evaluating the quality of a semen sample. The illustrated system 50 provides a true point-of-care cellphone-based semen analyzer that is easy-to-use, rapid, and inexpensive. The system 10 provides sperm concentration, motility, and linear and curvilinear velocities along with Hyaluronic Binding Assay (HBA) scores by performing image analysis on a mobile device 80. In the illustrated implementation, 3-D printing technology and laser cutting are utilized to inexpensively manufacture the hardware set up.

The optical system 60 comprises a light-emitting diode (LED) 62 configured to illuminate a sample inserted into the optical assembly 60. The LED 62 can be powered by either power source 64 placed within the housing, such as a watch battery, or through the cellphone. The optical assembly 60 further includes a first lens 66 and a second lens 68 positioned near an aperture of the optical assembly 60. In the illustrated example, the lenses 66 and 88 are both aspheric lenses with 4 and 27 mm focal lengths and numerical apertures of 0.43 and 0.16, respectively. In one implementation, the first lens 66 is a plano convex lens and the second lens 68 is a convexoconcave lens. The first lens 66 and the second lens 68 are positioned as to focus light from the light source through the aperture, with the lenses and the aperture defining an optical axis of the optical system.

In the illustrated implementation, the optical assembly 60 is housed in a 3-D printed, biodegradable Polylactic Acid (PLA) housing. In one example, the printed assembly weighs approximately twenty grams, not including the battery, and measures 6.1×8.3×3.1 cm. The housing is configured such that the lenses are aligned with a rear camera of the mobile device and, when the housing is in place, the lenses 66 and 68 are fixed in place at a distance appropriate for the focal length of the lenses. The cellphone's auto focus is utilized to achieve fine focusing.

A microfluidic-based chip 70 can be inserted into the housing of the optical assembly 60 for analysis of a semen-sample contained in the chip. The chip 70 comprises a self-loading mechanism 72 configured to draw semen into a reservoir 74 within the chip. In one implementation, the self-loading mechanism 72 includes a suction pump connected to an inlet through the reservoir 74. Due to the design of the microfluidic chip 70, the sample can comprise as little as ninety microliters. The microfluidic chip 70 has a disposable cap that is removed from the microchip before using it on phone for analysis, which eliminates any unwanted contamination.

In accordance with an aspect of the present invention, a portion of the surface of the reservoir is coated in an assay material 76, specifically Hyaluronan acid. Hyaluronic acid is major component of the matrix surrounding the human oocyte. They bind to mature sperms which are functionally competent in the zona pellucida. As will be discussed in detail below, the different behavior of the sperms in the region containing the assay material 76 and a region of the reservoir that does not contain the assay material can be utilized to estimate a percentage of mature and morphologically sound sperms within the sample. The microchips that will be used for the assay analysis have a shelf life of minimum two years at room temperature when stored in vacuum, dry plastic packaging. Trehalose, as a naturally occurring stabilization agent, can preserve multi-layered surfaces of immuno-functionalized microfluidic devices with immobilized proteins/antibodies for capturing CD4+ T lymphocytes to achieve long term storage at room temperature, and one implementation utilized trehalose for this purpose. In another implementation, the surface chemistry on the microchips is freeze-dried to prolong stability and shelf life of the microchips.

In one implementation, Hyaluronic acid coated coverglasses measuring 24×60 mm are used as the base substrate of the microchip. The coverglasses are custom coated with Hyaluronic acid in a 10×10 mm area, 10 mm away from the shorter edge of the glass. A laser cutter is used to cut 1.5 mm thick Poly(methyl methacrylate) (PMMA) which was used the top layer of the microchip. The inlet and outlet of the microchannels are cut in PMMA sheet using laser cutting. Double sided adhesive of 30 µm and 50 µm is used the channel layer and the channel (1×45 mm) is cut into it using the laser cutter. A 2 mL rubber bulb is attached to the channel forming a hermetic seal, capable of achieving suction. The double sided adhesive with the channel is sandwiched between the PMMA and the coverglass, and the edge containing the microchip's inlet is covered with a thin layer of latex to assist suction when used with the disposable cap. An extension on the disposable cap is constructed from micropipette tips and attached to the cap, such that the extension can be removed after semen is loaded into the reservoir.

Additional supplementary tests can also be merged with this system. For example, by providing an additional weighing scale which can weigh the semen sample and communicate the weight of the sample to the mobile device, the volume of semen produced by the patient can be obtained. An addition of a pH strip to the microchip can determine the pH value of the sample as well. The microchip 70 can also be augmented with the ability to check for specific biochemical markers using suitable surface chemistry. Such a simplified system capable providing a reliable diagnostic data can help users approach their own healthcare in a proactive manner.

It will be appreciated that the example assembly, as described, represents an economical alternative to conventional methods. The entire system can be constructed for less than five U.S. dollars in material costs not including the cost for a cellphone and labor charges. These costs include the lens system 66 and 68 (US$ 2), the 3-D printed polylactic acid housing (US$1.2), the LED 62 (US$ 0.09) and battery (US$ 0.60). The microchips which are used along with the device, will each cost around two dollars in material costs, accounting for the PMMA (~US$ 0.10), the double sided adhesive (~US$ 0.75), the PDMS based pump (~US$ 0.1) and the estimated cost of the HA coated slides should be US$ 1.

The mobile device 80 includes a camera 82, a processor 84, and a non-transitory computer readable medium 90 storing an application comprises executable instructions for evaluating a sperm quality from video captured at the camera. The software application was designed to provide a user-friendly interface for semen analysis. The application lets the user to take videos for analysis as well as archive previous tests and their reports. It was also designed as a platform for awareness, educating the user in the steps and parameters involved and on how to improve semen quality by suggesting possible lifestyle changes. It encourages the user to seek medical counselling when required. Hidden behind a simple user interface, the software makes use of a combination of various image processing algorithms and a custom developed tracking algorithm. The software is capable of providing velocity metrics, concentration, motility and HBA related data with the requirement of an external computational source. It also monitors the patient's result trend which might give an insight towards the effects of lifestyle and environmental changes.

A camera interface 91 is configured to instruct the camera to capture the video. It will be appreciated that this can be done in concert with the analysis of the semen sample, such that the analysis is performed substantially in real-time, or a recording can be stored for later analysis. A sperm recognition component 92 is configured to identify a plurality of individual sperms within each of a plurality of frames of the video. In one implementation, the sperm recognition component 92 uses an edge detection algorithm on each frame of video to recognize the individual sperms, such as Canny edge detection or a Sobel filter. Between the magnification provided by the optical assembly 60 and the edge detection algorithm, the sperm recognition component 92 can locate objects as small as three micrometers. The method is accurate for concentrations as low as fifty million cells per milliliter, and can be used for post-vasectomy analysis.

A sperm tracking component 94 is configured to map associated paths for a subset of the plurality of individual sperms across the plurality of frames of the video. In the illustrated implementation, the sperm tracking component 94 uses a recursive, fuzzy-logic based multiple object tracking algorithm to account for the Brownian-like motion exhibited by sperms. A mixture of Gaussian background subtraction can be used to ensure that only motile sperms are tracked by the system. By tracking the sperms across frames within the videos taken at the camera 82 at a known frame rate (e.g., frames per second), it is possible to calculate straight-line velocity (VSL), curvilinear velocity (VCL), and average path velocity (VAP) for each sample. The distance that the sperms traveled is calculated as a Gaussian distance. The cumulative distance computed between two continuous frames for a sperm cell is repeated till the end of the video.

An assay evaluation component 96 determines a percentage of sperms bound by the assay, and thus the percentage of morphologically sound and mature sperms. In the conventional method of analysis, the number of bound sperms is calculated manually, by looking at the sperm tails to check if they are beating vigorously. In the manual analysis, the tail motion is critical to be able to differentiate the live bound sperms from the dead ones. In the illustrated system 50, it is beyond its ability to be able to visualize the tail beating due to constraints in magnification and framerate. Accordingly, the software uses a different method for analysis. A number of motile sperms, $S_{assay}$, is determined in a region of the microfluidic chip containing the assay material, and a number of motile sperms, $S_{noassay}$, is determined in a region of the microfluidic chip not containing the assay material. The proportion of sperms that are immobilized by the assay material as $$\left(1 - \frac{S_{assay}}{S_{noassay}}\right).$$

Though this method of analysis relies on the assumption an equal population distribution exists in both regions, a surprisingly high degree of comparability was found with conventional methods.

A graphical user interface (GUI) 98 is configured to provide the results of the semen analysis to the user via a display of the mobile device. For example, the user interface can provide the total number of sperms, a concentration of sperm, a percentage or absolute number of motile sperms, an average linear and/or curvilinear velocity of the motile sperms, and a percentage of the sperms bound by the assay. In addition to an option to begin real-time analysis of a sample, the GUI 98 can provide an option where videos pre-recorded with the cellphone attachment can be analyzed and an option where the user can access the test history. The GUI 98 can also provide a questionnaire where general information about the patient is obtained prior to testing. The user can also gain access through the GUI 98 to further information on how to improve his semen health and the different parameters.

In one implementation, the application can provide feedback to the user based on the analysis on the massive data related to male fertility stored on a cloud system. The stored data may include geographical location, an average humidity and temperature, a humidity and temperature at the time of ejaculation, and user's habits such as smoking, alcohol consumption, etc. The user can utilize this feedback to adjust detrimental environmental or behavioral factors.

The system 50 provides an automated assay to quantify mature and morphologically superior sperms capable of achieving fertilization through use of microfluidic devices functionalized with hyaluronic acid (HA). This technology can be used as a home-based semen test, in satellite fertility clinics, and in point-of-care veterinary medicine. This platform technology also has other broad applications, including exploring microbial motility, performing low-cost microparticle image velocimetry, and detecting antibiotic resistance.

In addressing the problem of male infertility, the system 50 makes male fertility testing as accessible, easy, fast, and private as pregnancy tests for women. The system 50 provides an inexpensive, user-friendly cellphone-based microchip assay to rapidly measure sperm concentration, curvilinear and linear velocities, and total motility along with HBA scores using a semen sample of less than ten microliters. This technology can potentially change clinical decision making by providing private and inexpensive testing assay for earlier detection of the thirty percent of cases where the cause of infertility is solely the male or quickly rule out the male as the issue, which is true forty percent of the time. This will drastically speed up the clinical care process and eliminate unnecessary, expensive fertility testing for women in the thirty percent of cases that are completely attributable to the male. It will also significantly improve the patient (male and female) experience during this stressful time by providing them quick, cost-effective, and timely results with less stress.

Figure 3:
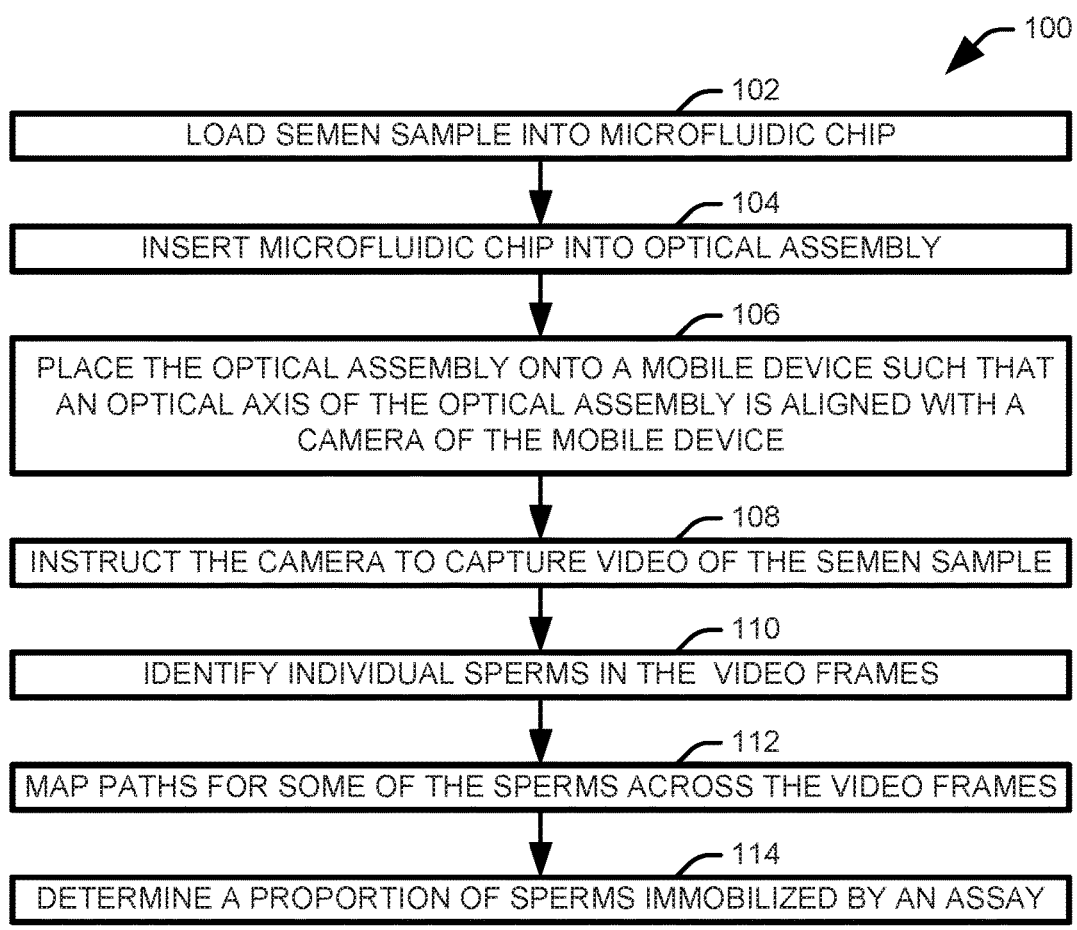
FIG. 3 illustrates one example of a method for evaluating the quality of a semen sample.

In view of the foregoing structural and functional features described above in FIGS. 1 and 2, example methods will be better appreciated with reference to FIG. 3. While, for purposes of simplicity of explanation, the method of FIG. 3 are shown and described as executing serially, it is to be understood and appreciated that the present invention is not limited by the illustrated order, as some actions could in other examples occur in different orders and/or concurrently from that shown and described herein.

FIG. 3 illustrates one example of a method 100 for evaluating the quality of a semen sample. At 102, the semen sample is loaded into a microfluidic chip. In one implementation, the semen sample is loaded via a suction pump attached to the chip. At 104, the microfluidic chip is inserted into an optical assembly. In one example, a housing of the optical assembly is configured to receive the microfluidic chip is aligned along an axis of the optical assembly. At 106, the optical assembly is placed onto a mobile device such that an optical axis of the optical assembly is aligned with a camera of the mobile device. In one implementation, the housing of the optical assembly is configured to mechanically affix to the mobile device.

At 108, the camera is instructed to capture video of the semen sample through the optical assembly. At 110, a plurality of individual sperms are identified within each of a plurality of frames of the video. In one example, an edge detection algorithm can be applied to assist in identification of individual sperms. At 112, associated paths for a subset of the plurality of individual sperms are mapped across the plurality of frames of the video. In one implementation, the paths for the subset of the plurality of individual sperms are mapped by applying a Mixture of Gaussian background subtraction algorithm across temporally adjacent frames to measure locations and trajectories of a plurality of motile sperms and providing the measured locations and trajectories to a recursive, fuzzy-logic based filter to determine the associated path for each of the plurality of motile sperms across the plurality of frames. From the mapped paths, each of a linear velocity and a curvilinear velocity can be determined for each of the subset of the plurality of individual sperms from the mapped paths for the subset of the plurality of individual sperms.

At 114, a proportion of sperms that are immobilized by an assay material selected to immobilize sperms is determined. In one implementation, each of a number of motile sperms, $S_{assay}$, in a region of the microfluidic chip containing the assay material and a number of motile sperms, $S_{noassay}$, in a region of the microfluidic chip not containing the assay material is determined. The proportion of sperms that are immobilized by the assay material are calculated as $$\left(1 - \frac{S_{assay}}{S_{noassay}}\right).$$

Figure 4:
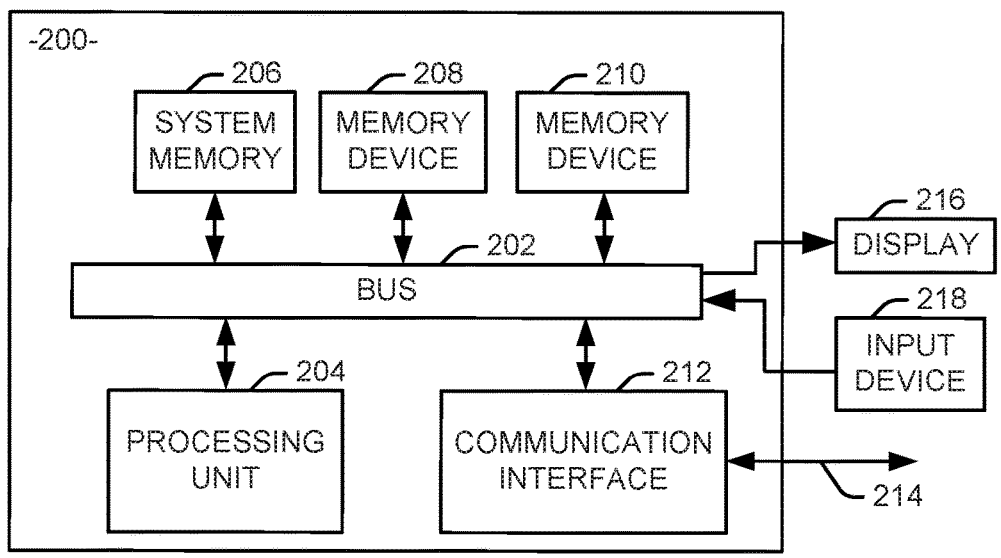
FIG. 4 is a schematic block diagram illustrating an exemplary system of hardware components capable of implementing examples of the systems and methods disclosed in FIGS. 1-3.

FIG. 4 is a schematic block diagram illustrating an exemplary system 200 of hardware components capable of implementing examples of the systems and methods disclosed in FIGS. 1-3. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a predictive modeling system in accordance with the present invention. Computer executable logic for implementing the composite applications testing system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. An assembly for evaluating the quality of a semen sample at a mobile device, the assembly comprising:
    an optical assembly comprising at least one lens;
    a housing configured to engage with the mobile device such that an axis of the optical assembly is substantially aligned with a camera of the mobile device, the optical assembly being contained within the housing;
    a microfluidic chip comprising a reservoir to hold the semen sample and configured to engage with the housing such that the reservoir is aligned with the axis of the optical assembly;
    a processor; and
    a non-transitory computer readable medium and storing executable instructions for evaluating a semen quality from video captured at the camera, the executable instructions comprising:
        a camera interface configured to instruct the camera to capture the video;
        a sperm recognition component configured to identify a plurality of individual sperms within each of a plurality of frames of the video; and
        a sperm tracking component configured to map associated paths for a subset of the plurality of individual sperms across the plurality of frames of the video and determine each of a linear velocity and a curvilinear velocity for each of the subset of the plurality of individual sperms from the mapped paths for the subset of the plurality of individual sperms.

2. The assembly of claim 1, the microfluidic chip comprising a self-loading mechanism comprising an extension for immersion in the semen sample and a pump for drawing semen into the reservoir.

3. The assembly of claim 2, wherein the extension is detachable from the microfluidic chip.

4. The assembly of claim 1, wherein at least a portion of the reservoir of the microfluidic chip is coated with Hyaluronic acid to immobilize mature sperms.

5. The assembly of claim 1, wherein the optical assembly comprises a light source and the at least one lens comprises a plano convex lens and a convexoconcave lens.

6. The assembly of claim 1, wherein the optical assembly comprises a plurality of aspheric lenses.

7. The assembly of claim 1, further comprising a scale configured to determine a weight of the semen sample.

8. The assembly of claim 1, the sperm recognition component being configured to apply an edge detection algorithm to each of the plurality of frames to identify the plurality of individual sperms.

9. The assembly of claim 1, the sperm tracking component utilizing a recursive filter to determine the associated path for each of the subset of the plurality of individual sperms across the plurality of frames.

10. The assembly of claim 1, wherein at least a portion of the reservoir of the microfluidic chip is coated with an assay material selected to immobilize mature sperms, and the executable instructions further comprise an assay evaluation component configured to determine a percentage of sperms immobilized by the assay material.

11. The assembly of claim 1, the executable instructions further comprising a user interface configured to provide a concentration of sperm with the semen sample, a concentration of motile sperm within the semen sample, total number of sperms in the sample, total number of motile sperms in the semen sample, and an average linear and curvilinear velocities of the motile sperms.

12. A method for evaluating the quality of a semen sample, comprising:
    loading the semen sample into a microfluidic chip;
    inserting the microfluidic chip into an optical assembly;
    placing the optical assembly onto a mobile device such that an optical axis of the optical assembly is aligned with a camera of the mobile device;
    instructing the camera to capture video of the semen sample through the optical assembly;
    identifying a plurality of individual sperms within each of a plurality of frames of the video;
    mapping associated paths for a subset of the plurality of individual sperms across the plurality of frames of the video; and
    determining each of a linear velocity and a curvilinear velocity for each of the subset of the plurality of individual sperms from the mapped paths for the subset of the plurality of individual sperms.

13. The method of claim 12, further comprising determining a proportion of sperms that are immobilized by an assay material selected to immobilize sperms.

14. The method of claim 13, wherein determining the proportion of sperms that are immobilized by the assay material comprises:
    determining a number of motile sperms, $S_{assay}$, in a region of the microfluidic chip containing the assay material;
    determining a number of motile sperms, $S_{noassay}$, in a region of the microfluidic chip not containing the assay material; and calculating the proportion of sperms that are immobilized by the assay material as $$\left(1 - \frac{S_{assay}}{S_{noassay}}\right).$$

15. The method of claim 12, wherein mapping associated paths for the subset of the plurality of individual sperms across the plurality of frames of the video comprises:
   apply a Mixture of Gaussian background subtraction algorithm across temporally adjacent frames to measure locations and trajectories of a plurality of motile sperms; and
   providing the measured locations and trajectories to a recursive filter to determine the associated path for each of the plurality of motile sperms across the plurality of frames.

16. A method for evaluating the quality of a semen sample, comprising:
   loading the semen sample into a microfluidic chip;
   inserting the microfluidic chip into an optical assembly;
   placing the optical assembly onto a mobile device such that an optical axis of the optical assembly is aligned with a camera of the mobile device;
   instructing the camera to capture video of the semen sample through the optical assembly;
   identifying a plurality of individual cells within each of a plurality of frames of the video;
   mapping associated paths for a subset of the plurality of individual cells across the plurality of frames of the video; and
   determining each of a linear velocity and a curvilinear velocity for each of the subset of the plurality of individual cells from the mapped paths for the subset of the plurality of individual cells.

17. An assembly for evaluating the quality of a semen sample, the assembly comprising:
   an optical assembly, contained within a housing and comprising at least one lens;
   a camera aligned with an axis of the optical assembly;
   a microfluidic chip comprising a reservoir to hold the semen sample, the housing being configured to engage with the housing such that the reservoir is aligned with the axis of the optical assembly;
   a processor; and
   a non-transitory computer readable medium and storing executable instructions for evaluating a semen quality from video captured at the camera, the executable instructions comprising:
      a camera interface configured to instruct the camera to capture the video;
      a sperm recognition component configured to identify a plurality of individual sperms within each of a plurality of frames of the video; and
      a sperm tracking component configured to map associated paths for a subset of the plurality of individual sperms across the plurality of frames of the video and determine each of a linear velocity and a curvilinear velocity for each of the subset of the plurality of individual sperms from the mapped paths for the subset of the plurality of individual sperms.

* * * * *